(12) United States Patent
Yamamoto et al.

(10) Patent No.: US 9,086,340 B2
(45) Date of Patent: Jul. 21, 2015

(54) TUBULAR INSERTION DEVICE

(71) Applicants: Olympus Corporation, Tokyo (JP); Olympus Medical Systems Corp., Tokyp (JP)

(72) Inventors: Eiji Yamamoto, Musashimurayama (JP); Ryo Tojo, Hachioji (JP); Jun Hane, Tokyo (JP); Jun Hasegawa, Hachioji (JP)

(73) Assignees: OLYMPUS CORPORATION, Tokyo (JP); OLYMPUS MEDICAL SYSTEMS CORP., Tokyo (JP)

(*) Notice: Subject to any disclaimer, the term of this patent is extended or adjusted under 35 U.S.C. 154(b) by 0 days.

(21) Appl. No.: 14/260,404

(22) Filed: Apr. 24, 2014

(65) Prior Publication Data

US 2014/0230562 A1    Aug. 21, 2014

Related U.S. Application Data

(63) Continuation of application No. PCT/JP2012/077764, filed on Oct. 26, 2012.

(30) Foreign Application Priority Data

Oct. 31, 2011    (JP) .................. 2011-238539

(51) Int. Cl.
| | |
|---|---|
| *G01L 1/24* | (2006.01) |
| *G01N 3/20* | (2006.01) |
| *A61B 1/005* | (2006.01) |
| *G02B 23/24* | (2006.01) |

(52) U.S. Cl.
CPC ............... *G01N 3/20* (2013.01); *A61B 1/0051* (2013.01); *G02B 23/2476* (2013.01)

(58) Field of Classification Search
USPC .......................................... 73/800
See application file for complete search history.

(56) References Cited

U.S. PATENT DOCUMENTS

| | | | | |
|---|---|---|---|---|
| 2008/0285909 | A1* | 11/2008 | Younge et al. | 385/13 |
| 2011/0172680 | A1* | 7/2011 | Younge et al. | 606/130 |
| 2013/0184567 | A1* | 7/2013 | Xie et al. | 600/424 |
| 2014/0275986 | A1* | 9/2014 | Vertikov | 600/424 |

FOREIGN PATENT DOCUMENTS

| | | |
|---|---|---|
| JP | 6-154153 A | 6/1994 |
| JP | 2001-169998 A | 6/2001 |

(Continued)

OTHER PUBLICATIONS

International Search Report dated Jan. 15, 2013 issued in PCT/JP2012/077764.

(Continued)

*Primary Examiner* — Lisa Caputo
*Assistant Examiner* — Jamel Williams
(74) *Attorney, Agent, or Firm* — Scully, Scott, Murphy & Presser, P.C.

(57) ABSTRACT

A tubular insertion device includes a tubular insertion portion including a flexible portion in a predetermined part, bending sensors distributed and arranged in the flexible portion, and an operation support information calculating unit. The operation support information calculating unit extracts operation support information including at least first external force information regarding an external force applied to the tubular insertion portion by a combinational calculation based on detection information from the bending sensors.

15 Claims, 12 Drawing Sheets

(56) References Cited

FOREIGN PATENT DOCUMENTS

| | | |
|---|---|---|
| JP | 2011-062291 A | 3/2011 |
| WO | WO 2010/050526 A1 | 5/2010 |

OTHER PUBLICATIONS

International Preliminary Report on Patentability and Written Opinion dated Jan. 15, 2013 received in related International Application No. PCT/JP2012/077764.

* cited by examiner

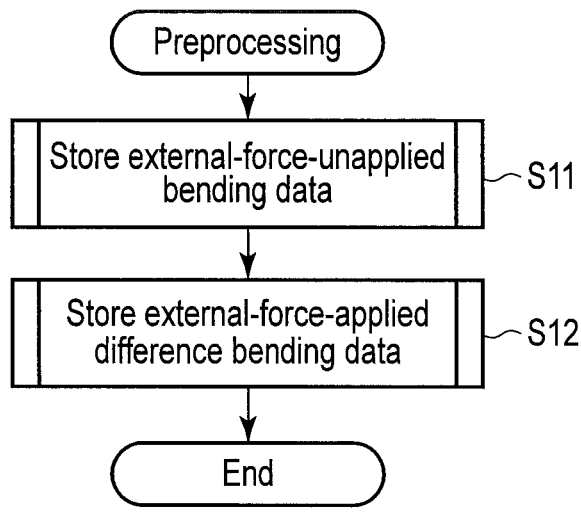
F I G. 3A
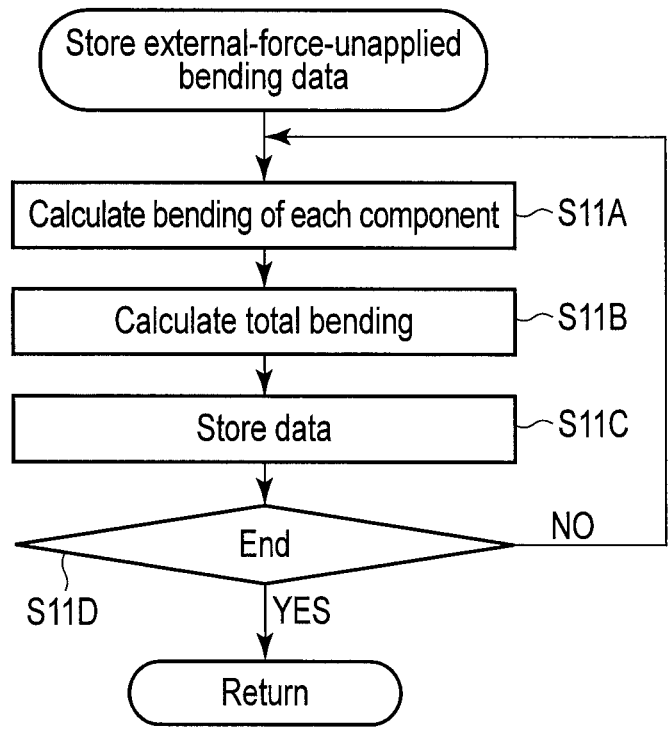
F I G. 3B

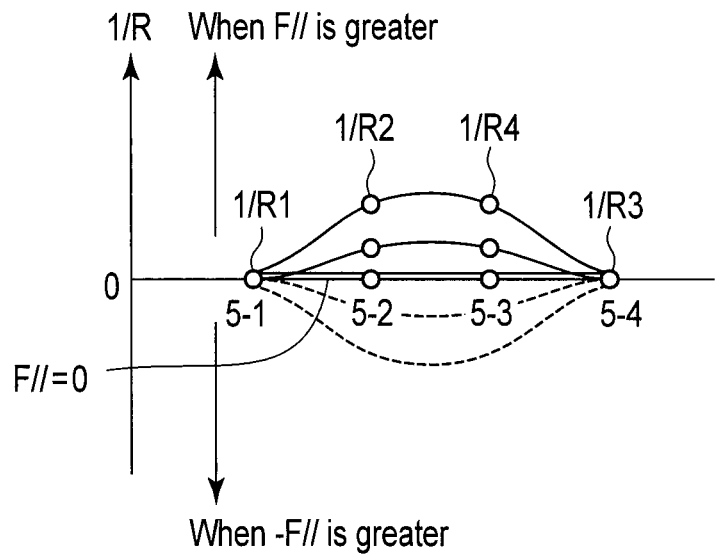
F I G. 5C
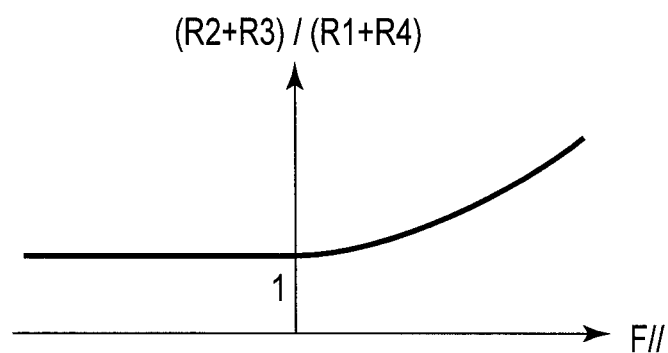
F I G. 5D

TUBULAR INSERTION DEVICE

CROSS-REFERENCE TO RELATED APPLICATIONS

This application is a Continuation Application of PCT Application No. PCT/JP2012/077764, filed Oct. 26, 2012 and based upon and claiming the benefit of priority from prior Japanese Patent Application No. 2011-238539, filed Oct. 31, 2011, the entire contents of all of which are incorporated herein by reference.

BACKGROUND OF THE INVENTION

1. Field of the Invention

The present invention relates to a tubular insertion device which comprises a tubular insertion portion including a flexible portion in a predetermined part.

2. Description of the Related Art

One known tubular insertion device in which a flexible cylindrical tube is inserted into a lumen is configured to detect the shape of the cylindrical tube by using an optical fiber for shape detection. For example, according to the disclosure in Jpn. Pat. Appln. KOKAI Publication No. 2001-169998, optical fibers for shape detection are arranged on the outer circumferential surface of a cylindrical tube so that bending detectors are located with predetermined intervals. These optical fibers are joined together in the longitudinal direction of the cylindrical tube to combine bending amounts of bending detection points so that the shape of the whole cylindrical tube can be detected.

Another known tubular insertion device in which a cylindrical tube is inserted into a lumen is configured so that a force sensor is disposed in the flexible cylindrical tube to detect an external force applied to the cylindrical tube. For example, according to a configuration shown in Jpn. Pat. Appln. KOKAI Publication No. 6-154153, strain gauges are arranged on the outer circumferential surface of a cylindrical tube to detect an external force applied to the outer circumferential surface of the cylindrical tube.

When the cylindrical tube is inserted into the lumen, the cylindrical tube is inserted while sometimes contacting the inner wall of the lumen. Therefore, when the lumen is rigid and twisting, there is a possibility that the distal end of the cylindrical tube may be worn and broken if the cylindrical tube is inserted by excessive force. When such lumen is soft, there is a possibility that the lumen may be damaged if the cylindrical tube is inserted by excessive force. To avoid this, it is preferable to know the external force applied to the cylindrical tube as operation support information when inserting the cylindrical tube.

According to Jpn. Pat. Appln. KOKAI Publication No. 2001-169998, although it is possible for an operator to know the shape of the tube as the operation support information regarding the cylindrical tube, it is not possible for the operator to know, for example, information regarding the external force applied to the tube. In the meantime, according to Jpn. Pat. Appln. KOKAI Publication No. 6-154153, it is possible to detect an external force applied to the tube from a particular direction. However, if the external forces applied to the tube from various directions are taken into consideration, it is necessary to attach a considerably large number of strain gauges. This leads to the following problems: the outer shape of the cylindrical tube is increased in size; the flexibility is hindered when a large number of wiring lines and sensors are attached; or a significant number of wiring lines for sensors are required.

BRIEF SUMMARY OF THE INVENTION

The present invention has been made in view of the above, and an object of the invention is to provide a tubular insertion device which enables external forces from all directions to be acquired as operation support information so that the size and rigidity of a tubular insertion portion are hardly affected when the tubular insertion portion having a flexible portion is inserted into a lumen.

According to an aspect of the present invention, a tubular insertion device includes: a tubular insertion portion including a flexible portion in a predetermined part; bending sensors distributed and arranged in the flexible portion; and an operation support information calculating unit configured to extract operation support information including at least first external force information regarding an external force applied to the tubular insertion portion by a combinational calculation based on detection information from the bending sensors.

According to another aspect of the present invention, a tubular insertion device includes: a tubular insertion portion including a flexible portion in a predetermined part; bending sensors distributed and arranged in the flexible portion; a bending operation unit for an operator to effect a bending condition of the tubular insertion portion; a bending operation detection sensor configured to detect an operation amount of the bending operation unit; and an operation support information calculating unit configured to extract operation support information including at least more than one piece of external force information regarding an external force applied to the tubular insertion portion by a combinational calculation based on detection information from the bending operation detection sensor and detection information from the bending sensors, and select or simultaneously use the external force information.

According to another aspect of the present invention, a tubular insertion device includes: a tubular insertion portion including a flexible portion in a predetermined part; a shape sensor which is disposed in the flexible portion and which detects a bending condition of the whole flexible portion; and an operation support information calculating unit configured to extract operation support information including at least external force information regarding external force applied to the tubular insertion portion by a combinational calculation based on detection information from the shape sensor in a condition in which no external force is applied to the tubular insertion portion and detection information from the shape sensor in a current condition.

According to the present invention, it is possible to provide a tubular insertion device which enables external forces from all directions to be acquired as operation support information so that the size and rigidity of a tubular insertion portion are hardly affected when the tubular insertion portion having a flexible portion is inserted into a lumen.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3A is a diagram showing a flowchart illustrating an operation procedure of a preprocessing operation in the operation support information calculating unit;

FIG. 3B is a diagram showing a flowchart illustrating an operation procedure of an external-force-unapplied bending data storing operation in the operation support information calculating unit;

FIG. 5C is a graph illustrating another example of an external force estimation method, and is a graph showing a distribution example of 1/curvature radius R for the bending detectors;

FIG. 5D is a graph illustrating another example of the external force estimation method, and is a graph showing an example of (R2+R3)/(R1+R4) for external force;

DETAILED DESCRIPTION OF THE INVENTION

Figure 1A:
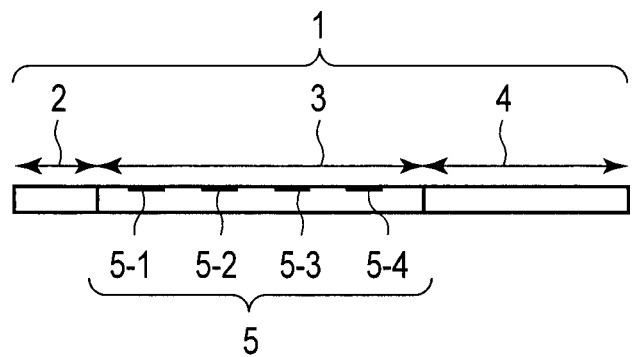
FIG. 1A is a diagram illustrating the principle of external force detection in a tubular insertion device according to a first embodiment of the present invention, and is a diagram showing a state in which an initial condition is straight and an external force is not applied.

Hereinafter, embodiments of the present invention will be described with reference to the drawings.

First Embodiment

First, the principle of external force detection in a tubular insertion device according to the first embodiment of the present invention is described with reference to FIG. 1A to FIG. 1H.

In the case described here, a tubular insertion portion 1 comprises a distal rigid portion 2, a flexible bending portion 3, and a quasi-rigid portion 4 in order from the distal end in the longitudinal direction as in, for example, an endoscope. The tubular insertion portion 1 is inserted into an unshown lumen by an operator. In the bending portion 3 which is a flexible portion, bending detectors 5-1, 5-2, 5-3, and 5-4 of a bending sensor as a bending detector 5 are distributed and arranged at predetermined intervals in the longitudinal direction. Alternatively, a shape sensor to detect the bending condition of the whole flexible portion of the bending portion 3 may be disposed as the bending detector 5.

Figure 1B:
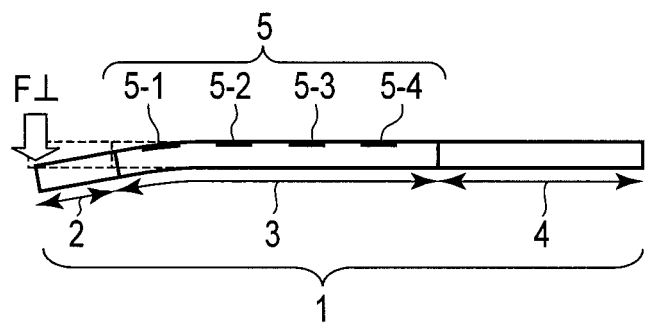
FIG. 1B is a diagram illustrating the principle of the external force detection in the tubular insertion device according to the first embodiment, and is a diagram showing a state in which the initial condition is straight and an external force is applied diagonally from the upper left side.
Figure 1C:
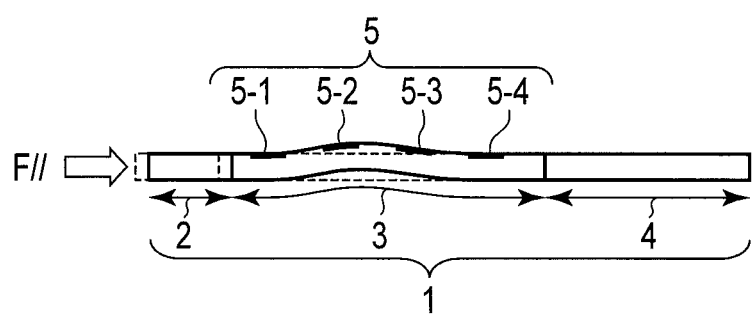
FIG. 1C is a diagram illustrating the principle of the external force detection in the tubular insertion device according to the first embodiment, and is a diagram showing a state in which the initial condition is straight and an external force is applied from the left front side.
Figure 1D:
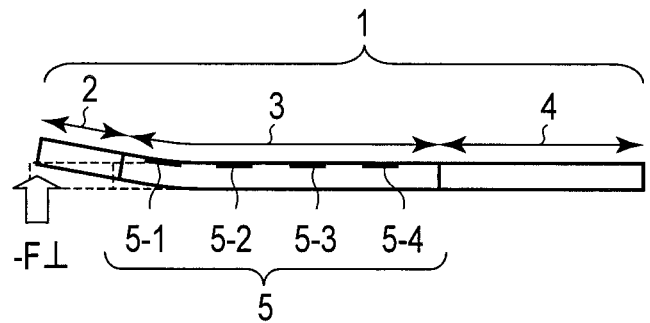
FIG. 1D is a diagram illustrating the principle of the external force detection in the tubular insertion device according to the first embodiment, and is a diagram showing a state in which the initial condition is straight and an external force is applied diagonally from the lower left side.

In the case shown in FIG. 1A, no external force is applied to the tubular insertion portion 1, and the bending portion 3 is straight. The condition shown in FIG. 1A is an initial straight condition. FIG. 1B shows a state of the tubular insertion portion 1 when an external force is applied to the distal end of the tubular insertion portion 1 diagonally from the upper left side of this drawing. FIG. 1C shows a state of the tubular insertion portion 1 when an external force is applied to the distal end of the tubular insertion portion 1 from the left front side of this drawing. FIG. 1D shows a state of the tubular insertion portion 1 when an external force is applied to the distal end of the tubular insertion portion 1 from the lower left side of this drawing.

In general, the distribution condition of bending variously changes depending on the distribution of the flexibility of the bending portion 3 and the external force. If the distribution of the flexibility of the bending portion 3 is known, the distribution condition of bending is determined by 1) the magnitude of the external force, 2) the direction of the external force, and a bending shape without the external force. For simplicity, the distribution of the flexibility of the bending portion 3 is uniform in the case discussed here. On this assumption, the bending amount (which may be considered in terms of angle or curvature) of the bending detector 5-1 located in the vicinity of the distal end is greater in the case of FIG. 1B. In the case of FIG. 1C, the bending amounts of the bending detectors 5-2 and 5-3 located in the vicinity of the center of the bending portion 3 are greater, and the bending portion 3 is shaped like a measuring worm. When the shape sensor is disposed instead of the bending sensors, the bending amounts in the vicinity of the center are also greater, and the bending portion 3 is also shaped like a measuring worm. In the case of FIG. 1D, the bending amount of the bending detector 5-1 located in the vicinity of the center of the bending portion 3 is greater in a direction opposite to the direction in the case of FIG. 1B.

Figure 1E:
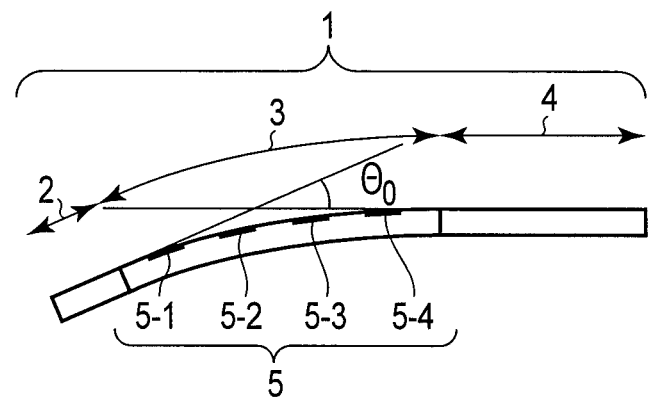
FIG. 1E is a diagram illustrating the principle of the external force detection in the tubular insertion device according to the first embodiment, and is a diagram showing a state in which an initial condition is bent and an external force is not applied.
Figure 1F:
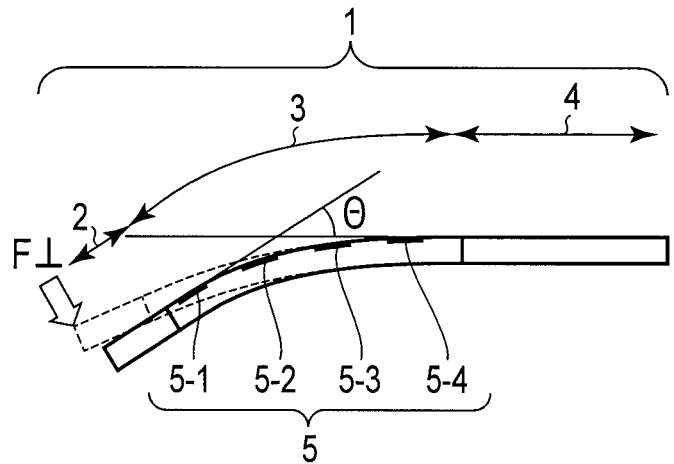
FIG. 1F is a diagram illustrating the principle of the external force detection in the tubular insertion device according to the first embodiment, and is a diagram showing a state in which an initial condition is bent and an external force is applied diagonally from the upper left side.
Figure 1G:
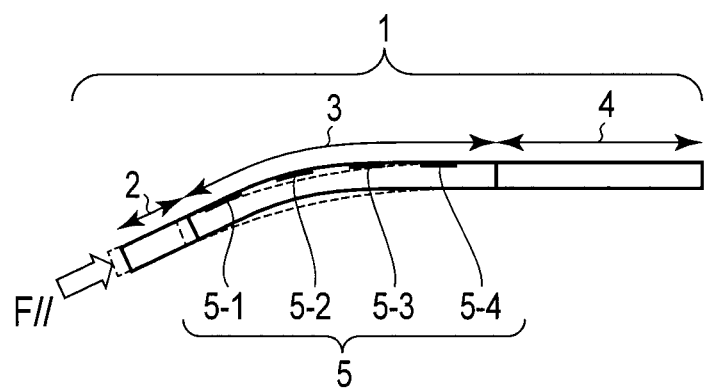
FIG. 1G is a diagram illustrating the principle of the external force detection in the tubular insertion device according to the first embodiment, and is a diagram showing a state in which an initial condition is bent and an external force is applied from the left front side.
Figure 1H:
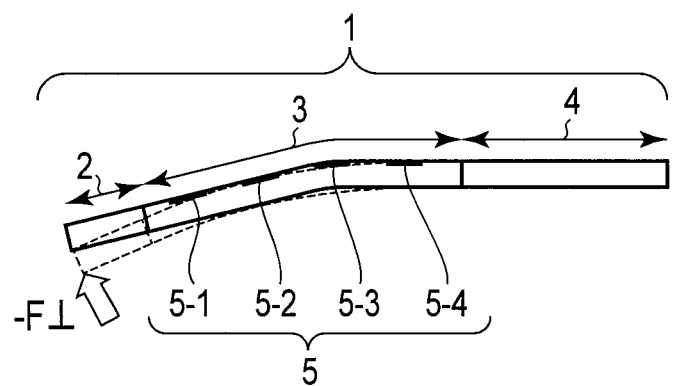
FIG. 1H is a diagram illustrating the principle of the external force detection in the tubular insertion device according to the first embodiment, and is a diagram showing a state in which an initial condition is bent and an external force is applied diagonally from the lower right side.

Similarly, FIG. 1E shows a state of the tubular insertion portion 1 in which the bending portion 3 is bent from the beginning when no external force is applied to the tubular insertion portion 1. FIG. 1F to FIG. 1H show states when an external force is further applied in this condition. Although not described in detail, a specific bending difference exists in the bending detectors 5-1, 5-2, 5-3, and 5-4 depending on the magnitude and direction of the external force as in the case described above. When the shape sensor is used, a specific bending difference also exists in the longitudinal direction.

Therefore, in contrast to the case in which no external force is applied, it is possible to detect the magnitude and direction of the external force applied to the distal end of the tubular insertion portion 1 by detecting the distribution (including the direction) of the curvatures of the bending detectors 5-1, 5-2, 5-3, and 5-4 of the bending sensors (note that the external force is not exclusively applied to the distal end of the tubular insertion portion 1). When the shape sensor is used, it is also possible to detect the direction and magnitude of the external force by the difference between the shape with the external force application and the shape without the external force application.

An example of a signal processing algorithm for detecting the external force is now described in detail (note that the present invention is not limited to the example of the following algorithm).

Figure 2:
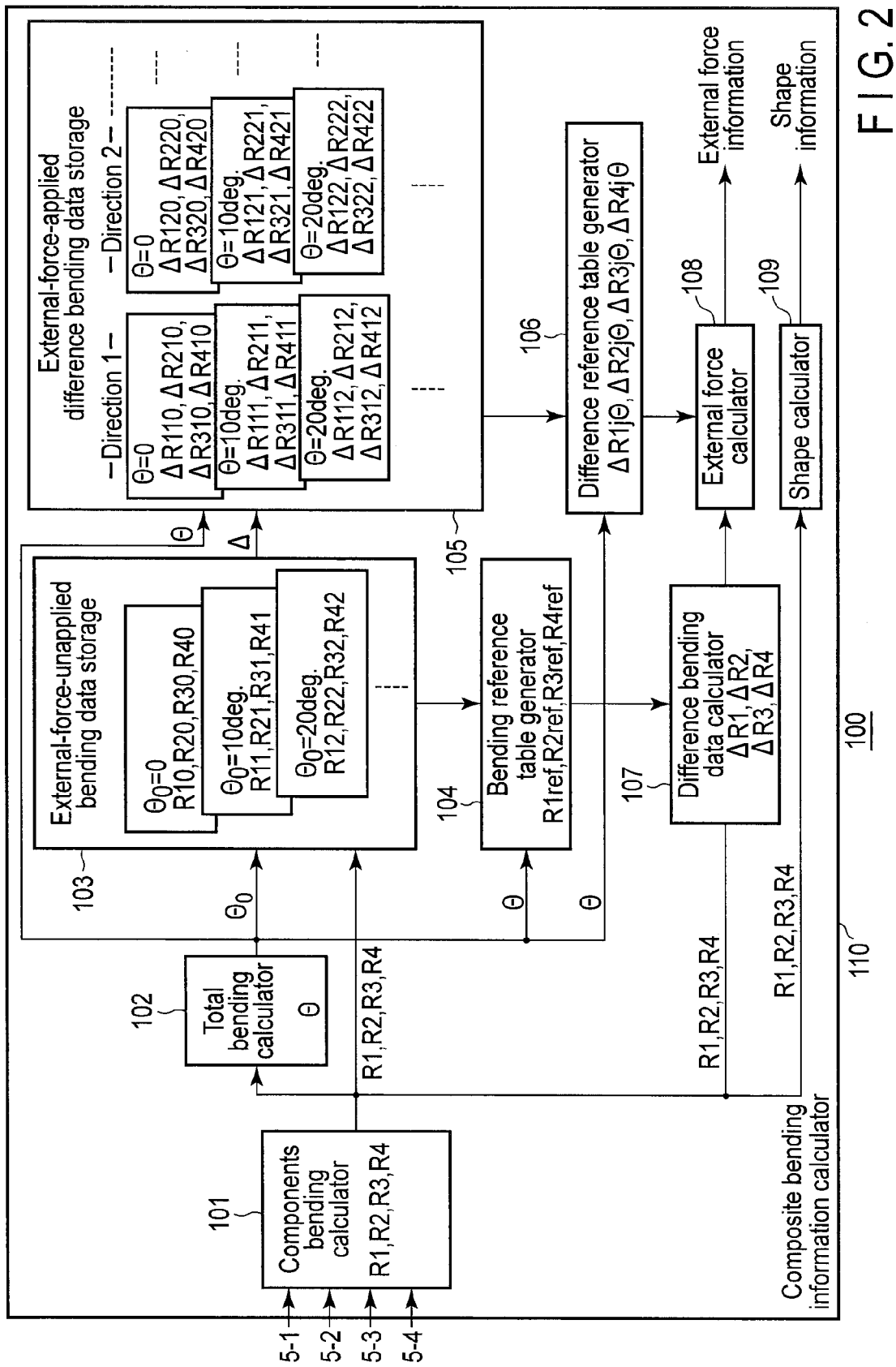
FIG. 2 is a diagram showing the configuration of an operation support information calculating unit in the tubular insertion device according to the first embodiment.

The tubular insertion device according to the present embodiment comprises an operation support information calculating unit 100 having a configuration shown in FIG. 2. The operation support information calculating unit 100 has a composite bending information calculator 110 which comprises a components bending calculator 101, a total bending calculator 102, an external-force-unapplied bending data storage 103, a bending reference table generator 104, an external-force-applied difference bending data storage 105, a difference reference table generator 106, a difference bending data calculator 107, an external force calculator 108, and a shape calculator 109.

The input of the components bending calculator 101 is connected to each of the bending sensors comprising the bending detectors 5-1, 5-2, 5-3, and 5-4. The output of the components bending calculator 101 is connected to the total bending calculator 102, the external-force-unapplied bending data storage 103, the difference bending data calculator 107, and the shape calculator 109. The output of the total bending calculator 102 is connected to the external-force-unapplied bending data storage 103, the bending reference table generator 104, the external-force-applied difference bending data storage 105, and the difference reference table generator 106. The output of the external-force-unapplied bending data storage 103 is connected to the bending reference table generator 104 and the external-force-applied difference bending data storage 105. The output of the bending reference table generator 104 is connected to the difference bending data calculator 107. The output of the external-force-applied difference bending data storage 105 is connected to the difference reference table generator 106. The output of the difference reference table generator 106 is connected to the external force calculator 108. The output of the external force calculator 108 is output to the outside of the operation support information calculating unit 100 as external information. The output of the shape calculator 109 is output to the outside of the operation support information calculating unit 100 as shape information.

The operation of each component is described below with reference to flowcharts shown in FIG. 3A to FIG. 3C and FIG. 4. First, a preprocessing operation to store data in the external-force-unapplied bending data storage 103 and the external-force-applied difference bending data storage 105 is described.

That is, in the preprocessing operation, as shown in FIG. 3A, an external-force-unapplied bending data storing process is first performed to find the curvature from each of the bending detectors 5-1, 5-2, 5-3, and 5-4 for each total bending angle of the tubular insertion portion 1 without an external force (the method is not limited), and store the curvature in the external-force-unapplied bending data storage 103 (step S11). External-force-applied difference bending data storing processing is then performed. In the external-force-applied difference bending data storing processing, the curvature in each of the bending detectors 5-1, 5-2, 5-3, and 5-4 is measured with the application of predetermined external force Fo to the distal end (not limited to this part) of the tubular insertion portion 1 from all considered directions, and the difference between the bending data with the external force application and the bending data without the external force application is then recorded in the external-force-applied difference bending data storage 105 (step S12).

In the external-force-unapplied bending data storing processing performed in step S11, as shown in FIG. 3B, a components bending calculation is first performed by the components bending calculator 101 to calculate curvatures R1, R2, R3, and R4 of the bending detectors from detection signals output from the bending sensors comprising the bending detectors 5-1, 5-2, 5-3, and 5-4 without an external force (step S11A). A total bending calculation is then performed by the total bending calculator 102 to geometrically find a total bending angle θ0 (which may be a converted curvature) of the tubular insertion portion 1 in accordance with the curvatures R1, R2, R3, and R4 of the respective components and the spacing of the bending detectors (step S11B). This total bending angle θ0 is indicated as θ0 in FIG. 1E. The calculated curvatures R1, R2, R3, and R4 in the bending detectors 5-1, 5-2, 5-3, and 5-4 are stored in the external-force-unapplied bending data storage 103 as bending data Rik (i: detection point number, k: the number corresponding to the degree of total bending) to correspond to the found total bending angle θ0 (step S11C). Whether the external-force-unapplied bending data storing processing has ended is then determined (step S11D). When the external-force-unapplied bending data storing processing has not ended yet, the procedure returns to step S11A, and the operation for the next total bending angle is repeated.

The end determination in step S11D may be performed by determining whether the operator has performed an end operation using an unshown input unit, or may be automatically performed by determining whether a prescribed operation regarding the number of data and the angle has been finished. The components bending calculation in step S11A may also be performed by determining whether the operator has performed a calculation start operation using the unshown input unit, or may be performed at prescribed time intervals that allow the total bending angle of the tubular insertion portion 1 to be changed by some means.

In the example shown in FIG. 2, the total bending angle θ0 of the tubular insertion portion 1 without the external force application is set at 0 degrees, 10 degrees, 20 degrees, . . . by some means, and the curvatures R1, R2, R3, and R4 of the bending detectors 5-1, 5-2, 5-3, and 5-4 calculated for each total bending angle θ0 are stored as the bending data Rik. That is, when the total bending angle θ0 is 0 degrees, the calculated curvatures R1, R2, R3, and R4 are stored as bending data R10, R20, R30, and R40. When the total bending angle θ0 is 10 degrees, the calculated curvatures R1, R2, R3, and R4 are stored as bending data R11, R21, R31, and R41. When the total bending angle θ0 is 20 degrees, the calculated curvatures R1, R2, R3, and R4 are stored as bending data R12, R22, R32, and R42.

Figure 3C:
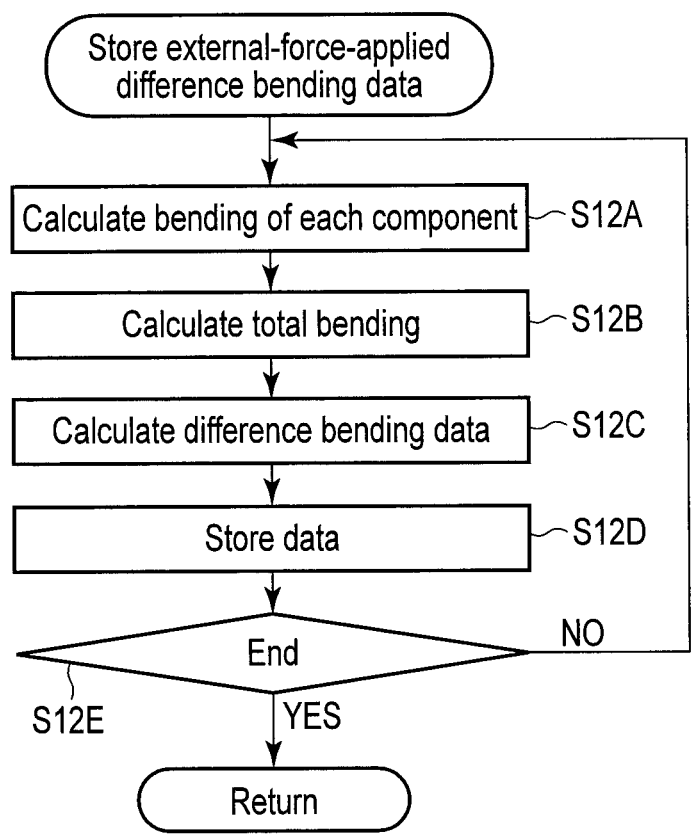
FIG. 3C is a diagram showing a flowchart illustrating an operation procedure of an external-force-applied difference bending data storing operation in the operation support information calculating unit.

In the external-force-applied difference bending data storing processing performed in step S12, as shown in FIG. 3C, a components bending calculation is first performed by the components bending calculator 101 to calculate the curvatures R1, R2, R3, and R4 of the bending detectors from detection signals output from the bending sensors comprising the bending detectors 5-1, 5-2, 5-3, and 5-4 when the external force Fo in a predetermined direction is applied to the distal end (not limited to this part) of the tubular insertion portion 1 (step S12A). A total bending calculation is then performed by the total bending calculator 102 to geometrically find a total bending angle θ0 (which may be a converted curvature) of the tubular insertion portion 1 in accordance with the curvatures R1, R2, R3, and R4 of the respective components and the spacing of the bending detectors (step S12B). This total bending angle θ is indicated as θ in FIG. 1F. The difference between the bending data Rik with the external force application and the bending data Rik without the external force application is further found to calculate difference bending data ΔRijk (i: detection point number, j: external force direction number, k: the number corresponding to the degree of total bending) (step S12C). The calculated difference bending data ΔRijk is recorded in the external-force-applied difference bending data storage 105 to correspond to the found total bending angle θ (step S12D). Whether the external-force-applied difference bending data storing processing has ended is then determined (step S12E). When the external-force-applied difference bending data storing processing has not ended yet, the procedure returns to step S12A, and the operation for the next total bending angle or the operation for the direction of the application of the external force Fo is repeated.

The end determination in step S12E may be performed by determining whether the operator has performed an end operation using the unshown input unit, or may be automatically performed by determining whether a prescribed operation regarding the number of data, the angle, and the external force has been finished. The components bending calculation in step S12A may also be performed by determining whether the operator has performed a calculation start operation using the unshown input unit, or may be performed at prescribed time intervals that allow the total bending angle of the tubular insertion portion 1 or the direction of the application of the external force Fo to be changed by some means.

In the example shown in FIG. 2, the total bending angle θ of the tubular insertion portion 1 without the external force application is set at 0 degrees, 10 degrees, 20 degrees, . . . , and the difference bending data ΔRijk obtained when the external force Fo which is changed in direction is applied to the distal end (not limited to this part) of the tubular insertion portion 1 for each total bending angle θ is stored. That is, when the total bending angle θ is 0 degrees, the difference bending data ΔRijk is stored as difference bending data ΔR110, ΔR210, ΔR310, and ΔR410 if the external force Fo in a direction 1 is applied, or the difference bending data ΔRijk is stored as difference bending data ΔR120, ΔR220, ΔR320, and ΔR420 if the external force Fo in a direction 2 is applied. When the total bending angle θ is 10 degrees, the difference bending data ΔRijk is stored as difference bending data ΔR111, ΔR211, ΔR311, and ΔR411 if the external force Fo in the direction 1 is applied, or the difference bending data ΔRijk is stored as difference bending data ΔR121, ΔR221, ΔR321, and ΔR421 if the external force Fo in the direction 2 is applied. When the total bending angle θ is 20 degrees, the difference bending data ΔRijk is stored as difference bending data ΔR112, ΔR212, ΔR312, and ΔR412 if the external force Fo in the direction 1 is applied, or the difference bending data ΔRijk is stored as difference bending data ΔR122, ΔR222, ΔR322, and ΔR422 if the external force Fo in the direction 2 is applied.

Here, for simplicity of explanation, the difference bending data ΔRijk is found and stored for each total bending angle and for each direction of the application of the external force Fo. However, it is actually preferable that the difference bending data ΔRijk is found and stored for each magnitude of the external force or for each combination of the direction and magnitude of the external force Fo.

It is preferable that the preprocessing operation described above is performed at least before the stage in which the user actually starts using the tubular insertion device; for example, during the manufacture at a factory or during an inspection before shipment, and the data is then stored in the external-force-unapplied bending data storage 103 and the external-force-applied difference bending data storage 105. However, each component changes in quality due to the use of the tubular insertion device, thus these data need to be updated at a certain timing. This timing can be, for example, every time power is applied to the tubular insertion device, every time power has been applied a predetermined number of times, or upon predetermined regular maintenance.

A normal operation during the use of the tubular insertion device by the user is described next. Now, suppose that the operator who is the user operates the tubular insertion portion 1 and inserts the tubular insertion portion 1 into the lumen.

Figure 4:
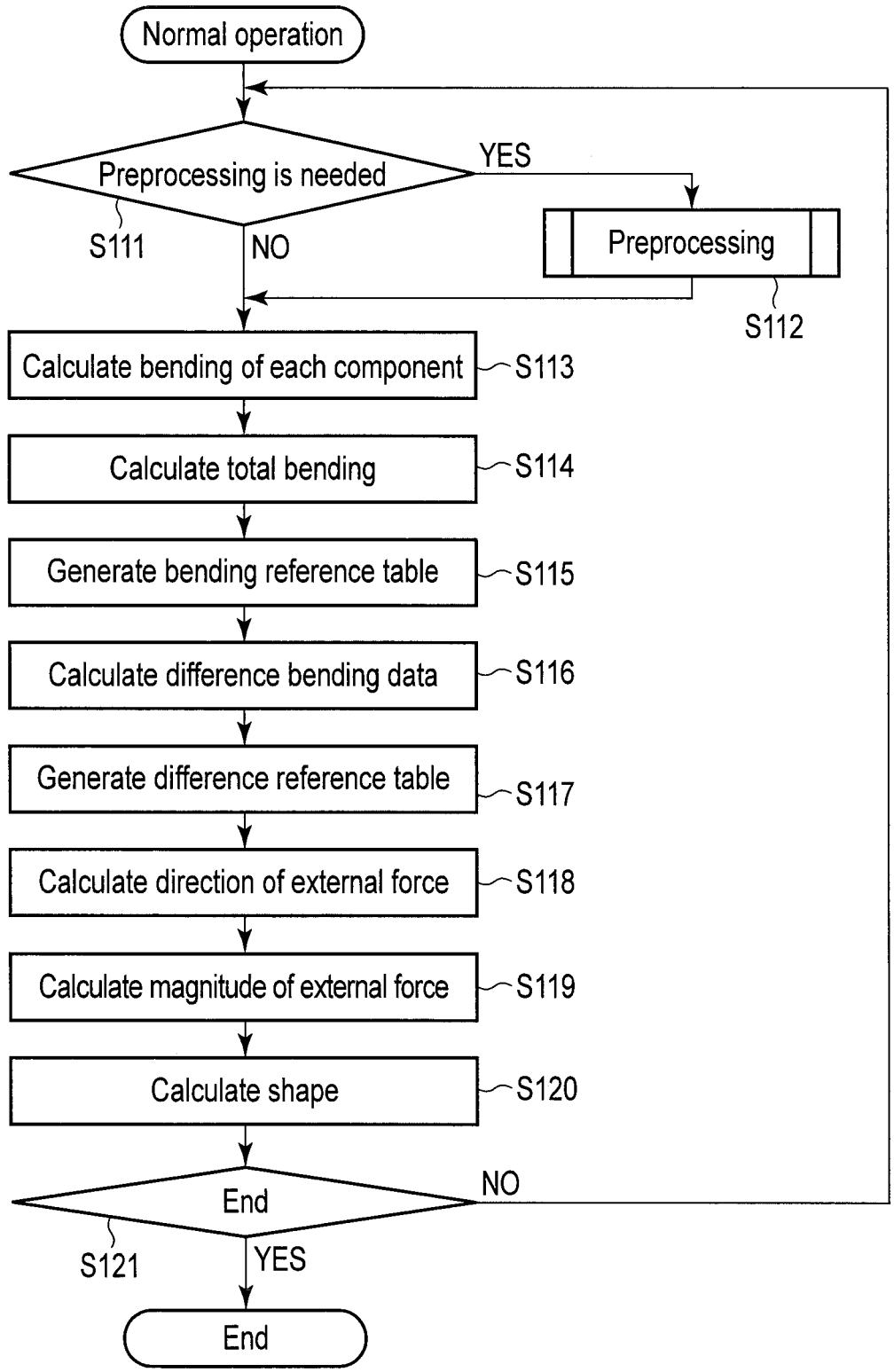
FIG. 4 is a diagram showing a flowchart illustrating an operation procedure of a normal operation in the operation support information calculating unit.

As shown in FIG. 4, whether the preprocessing operation described above needs to be performed is first ascertained (step S111). This determination is based on, for example, whether the data is stored in the external-force-unapplied bending data storage 103 and the external-force-applied difference bending data storage 105 or whether the above-mentioned certain timing has been reached even if the data is stored. The result of this ascertainment may be input by the operator using the unshown input unit, or may be automatically acquired by an unshown controller which controls the operation of each component in the operation support information calculating unit 100. When the preprocessing operation needs to be performed, the preprocessing operation described above is performed (step S112).

When the preprocessing operation does not need to be performed or after the preprocessing operation has been performed, the components bending calculation is performed by the components bending calculator 101 to calculate the curvatures R1, R2, R3, and R4 of the bending detectors from detection signals output from the bending sensors comprising the bending detectors 5-1, 5-2, 5-3, and 5-4 (step S113). The total bending calculation is then performed by the total bending calculator 102 to geometrically find a current total bending angle θ of the tubular insertion portion 1 in accordance with the curvatures R1, R2, R3, and R4 of the respective components and the spacing of the bending detectors (step S114). Bending reference data Riref without the external force application is then generated by the bending reference table generator 104 in accordance with the total bending angle θ obtained as described above (step S115). That is, on the basis of the current total bending angle θ0 found by the total bending calculator 102, the bending reference table generator 104 refers, from the external-force-unapplied bending data storage 103, the bending data Rik corresponding to the total bending angle θ0 without the external force application proximate to the current total bending angle θ. Further, the referred bending data Rik is preferably interpolated into the current total bending angle θ to calculate reference bending data R1ref, R2ref, R3ref, and R4ref of the bending detectors 5-1, 5-2, 5-3, and 5-4 corresponding to the current total bending angle θ.

A difference bending data calculation is then performed by the difference bending data calculator 107 to find difference bending data ΔRi (step S116). That is, the difference bending data calculator 107 performs the following difference calculation by using the curvatures R1, R2, R3, and R4 of the bending detectors 5-1, 5-2, 5-3, and 5-4 found by the components bending calculator 101 and using the reference bending data R1ref, R2ref, R3ref, and R4ref without the external force application of the bending detectors 5-1, 5-2, 5-3, and 5-4 generated by the bending reference table generator 104, thereby finding reference bending data ΔR1, ΔR2, ΔR3, and ΔR4.

$$\Delta R1 = R1 - R1\mathrm{ref},$$

$$\Delta R2 = R2 - R2\mathrm{ref},$$

$$\Delta R3 = R3 - R3\mathrm{ref},$$

$$\Delta R4 = R4 - R4\mathrm{ref}.$$

Reference difference data ΔRijθ is generated by the difference reference table generator 106 (step S117). That is, on the basis of the current total bending angle θ found by the total bending calculator 102, the difference reference table generator 106 refers, from the external-force-applied difference bending data storage 105, the difference bending data ΔRijk corresponding to the total bending angle θ with the external force application proximate to the current total bending angle θ. Further, the referred difference bending data ΔRijk is preferably interpolated into the current total bending angle θ to calculate reference difference data ΔR1jθ, ΔR2jθ, ΔR3jθ, and ΔR4jθ corresponding to the current total bending angle θ.

The principle described with reference to FIG. 1 is then used by the external force calculator 108 to calculate the direction and magnitude of the current external force F (step S118 and step S119).

That is, the external force calculator 108 selects a set proximate in ratio to a set of difference values of a current bending distribution (the difference bending data ΔR1, ΔR2, ΔR3, and ΔR4) extracted by the difference bending data calculator 107, for example, from among sets of difference values (the reference difference data ΔR1jθ, ΔR2jθ, ΔR3jθ, and ΔR4jθ (j=1, 2, 3, . . . )) calculated by the difference reference table generator 106. As a result, "j" of the set having the closest ratio is determined, and the direction of the external force corresponding to this "j" is extracted as the direction of the current external force. It is particularly preferable to extract sets having close ratios instead of the above-mentioned set having the proximate ratio, and interpolate the direction of the corresponding external force to extract the direction of the current external force F.

The external force calculator 108 multiplies the ratio of magnitude between the set of difference values of the current bending distribution (the difference bending data ΔR1, ΔR2, ΔR3, and ΔR4) extracted by the difference bending data calculator 107 and the set of difference values (the reference difference data ΔR1jθ, ΔR2jθ, ΔR3jθ, and ΔR4jθ (j is determined at this point)) provided by the difference reference table generator 106, by the external force Fo previously set when the data has been stored in the external-force-applied difference bending data storage 105, thereby estimating the magnitude of the external force F. For example, the following calculation can be performed:

$$F = Fo \times Avr(\Delta R1, \Delta R2, \Delta R3, \Delta R4)/Avr(\Delta R1j\theta, \Delta R2j\theta, \Delta R3j\theta, \Delta R4j\theta).$$

Here, Avr (an argument 1, an argument 2, . . . ) indicates an averaging calculation of the argument 1, the argument 2, . . . , and can be a simple average, a root mean square, or a weighted average. Which average calculation to select is preferably determined by, for example, experimentally ascertaining the best suited calculated method in accordance with the structure of the tubular bending portion 3 to be detected and environmental conditions.

Furthermore, the shape calculator 109 joins together the curvatures R1, R2, R3, and R4 of the bending detectors 5-1, 5-2, 5-3, and 5-4 in consideration of the spacing of the bending detectors, and thereby calculates shape information regarding the whole tubular insertion portion 1 (step S120).

In this way, the operation support information including external force information (direction and magnitude) regarding the external force F applied to the tubular insertion portion 1 and the shape information regarding the shape of the tubular insertion portion 1 is obtained.

The end of the normal operation is then determined (step S121). When the normal operation has not ended yet, the procedure returns to step S111, and the operation for finding the next operation support information is repeated.

The end determination in step S121 is performed by determining whether the operator has performed an end operation using the unshown input unit. Alternatively, the end determination in step S121 may not be particularly performed, and the procedure may return to step Sill from step S120, and the normal operation may be ended by turning off the power of the tubular insertion device.

As described above, in the tubular insertion device according to the present first embodiment, when the tubular insertion portion 1 having, in a predetermined part, the bending portion 3 which is the flexible portion is inserted into the lumen, the operation support information calculating unit 100 as an operation support information calculator extracts the operation support information including the external force information regarding the external force applied to at least the tubular insertion portion 1 by a combinational calculation of detection information in the bending sensors distributed and arranged in the bending portion 3 or by a combinational calculation of detection information from the shape sensor disposed in the bending portion 3 in a condition in which no external force is applied to the tubular insertion portion 1 and detection information from the shape sensor in the current situation. Thus, it is possible to acquire external forces from all directions as the operation support information so that the size and rigidity of the tubular insertion portion 1 are hardly affected. Moreover, the shape of the tubular insertion portion 1 can also be acquired as the operation support information.

The following methods can also be used as a method of estimating the direction and magnitude of the current external force F.

Figure 5A:
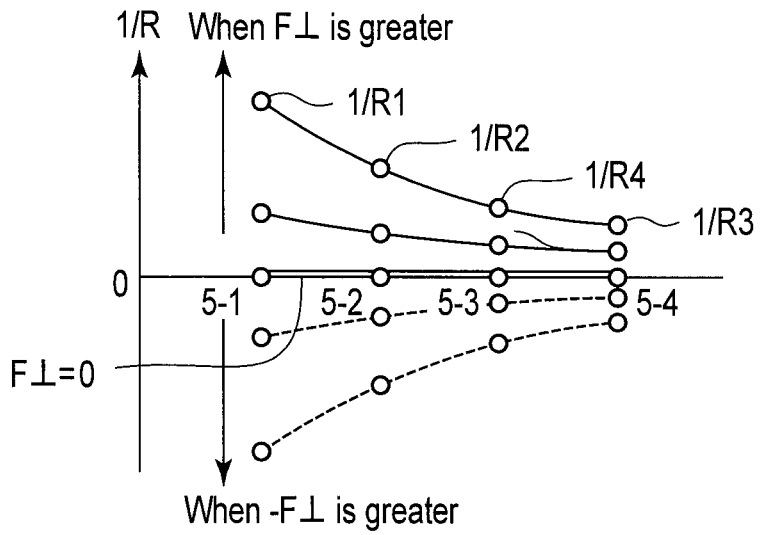
FIG. 5A is a graph illustrating another example of an external force estimation method, and is a graph showing a distribution example of 1/curvature radius R for bending detectors.

FIG. 5A shows a distribution example of a "1/curvature radius R" in the bending detectors 5-1, 5-2, 5-3, and 5-4 when the external force varies in direction and magnitude in the case where the condition of the tubular insertion portion 1 is as shown in FIG. 1A to FIG. 1D. Here, the curvature radiuses of the bending detectors 5-1, 5-2, 5-3, and 5-4 are R1, R2, R3, and R4, respectively, and the curvature radius is + in the case of upward projection as shown in FIG. 1B, whereas the curvature radius is − in the case of downward projection. F// indicates the magnitude (a direction to the insertion portion 1 is +) of the force applied to the distal end of the tubular insertion portion 1 in the length direction of the tubular insertion portion 1. F⊥ indicates the magnitude of the force applied to the distal end of the tubular insertion portion 1 in a direction perpendicular to the length direction (a downward application direction in the drawing is +).

Figure 5B:
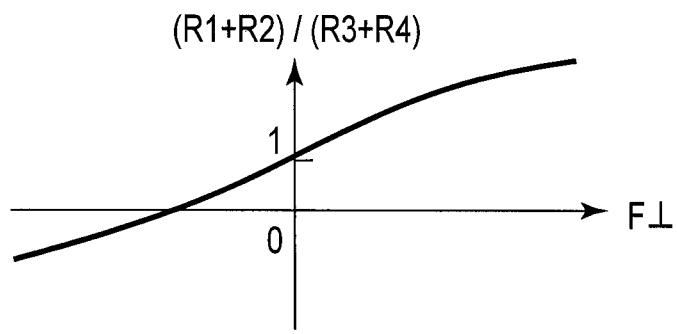
FIG. 5B is a graph illustrating another example of the external force estimation method, and is a graph showing an example of (R1+R2)/(R3+R4) for external force.

For simplicity, suppose that total bending angle θ0 without the external force application is equal to 0, the elasticity of the bending portion 3 is uniform, and the bending detectors 5-1, 5-2, 5-3, and 5-4 are uniformly arranged at regular intervals. In this case, the force F⊥ applied in the direction perpendicular to the length direction is used as a parameter, so that the distribution example of the "1/curvature radius R" in the bending detectors 5-1, 5-2, 5-3, and 5-4 is as shown in FIG. 5A. That is, when the external force is applied to the distal end, the absolute value of the curvature (1/R) is higher in a part closer to the distal end of the tubular insertion portion 1. For example, (R1+R2)/(R3+R4) is taken as the index of a curvature distribution as shown in FIG. 5B. Therefore, if (R1+R2)/(R3+R4) is known, it is possible to estimate F⊥ which is a force component applied in the direction perpendicular to the length direction of the tubular insertion portion 1.

On the other hand, a distribution example of the "1/curvature radius R" in the bending detectors 5-1, 5-2, 5-3, and 5-4 when the force F// applied in the length direction is used as a parameter is as shown in FIG. 5C. That is, when the external force is applied to the distal end, the tubular insertion portion 1 is shaped to be bent in the center. Accordingly, for example, (R2+R3)/(R1+R4) is taken as the index of a curvature distribution as shown in FIG. 5D. Therefore, if (R2+R3)/(R1+R4) is known, it is possible to estimate F// which is a force component applied in the length direction of the tubular insertion portion 1.

To sum up, the values of the above-mentioned indexes (R1+R2)/(R3+R4) and (R2+R3)/(R1+R4) with the external force application and without the external force application are previously checked at every total bending angle θ0 without the external force application, and are stored in the external-force-unapplied bending data storage 103 and the external-force-applied difference bending data storage 105. Consequently, it is possible to estimate the external force components F⊥ and F// (i.e., estimate the direction and magnitude of the external force).

Figure 6:
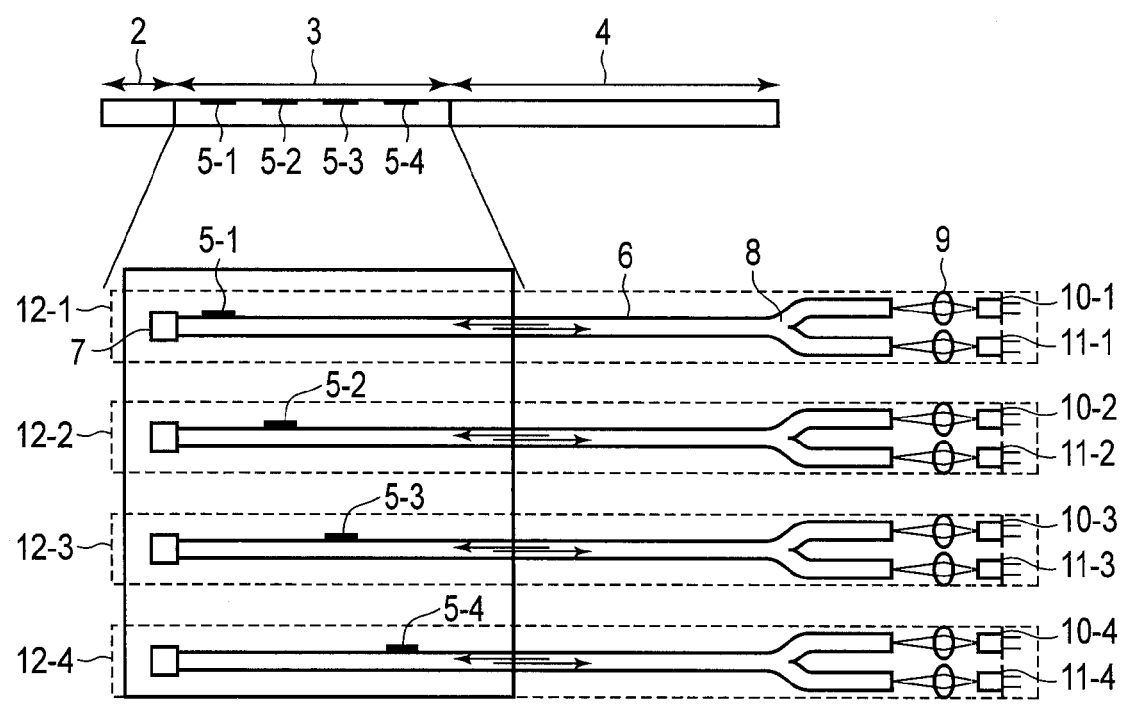
FIG. 6 is a diagram showing a configuration example of a bending sensor including the bending detectors.

As the bending sensors comprising the bending detectors 5-1, 5-2, 5-3, and 5-4, it is possible to use fiber bending sensors 12-1, 12-2, 12-3, and 12-4 which use the bending loss of the optical fiber as shown in FIG. 6.

That is, the input end of an optical fiber 6 comprises a branch structure 8 in each of the fiber bending sensors 12-1, 12-2, 12-3, and 12-4. Light emitted from light sources 10-1, 10-2, 10-3, and 10-4 enters one end of the branch via a lens 9. The light is guided by the optical fiber 6, and reflected by a mirror 7 disposed at the distal end. The reflected light again travels through the optical fiber 6, the branch structure 8, and the lens 9, and is detected by photodetectors 11-1, 11-2, 11-3, and 11-4. Here, along the light guide path of the optical fiber 6, light loss units functioning as the bending detectors 5-1, 5-2, 5-3, and 5-4 are formed in the vicinity of the outer circumference of the light guide path. When the optical fiber 6 is bent, it is possible to detect a bending amount by using the light loss amounts of the light loss units which vary with the degree of the bending.

Regarding the fiber bending sensors, the bending detectors 5-1 to 5-4 are staggered in the longitudinal direction of the bending portion 3. Thus, detection results from the bending detectors 5-1 to 5-4 can be used to detect a bending distribution in the longitudinal direction.

When there is a distribution of the level of the flexibility of the bending portion 3, it is preferable to optimally set the spacing of the bending detectors 5-1 to 5-4 and the sensitivities of the bending detectors 5-1 to 5-4. The present invention also includes a configuration in which bending detectors are continuously distributed instead of the bending sensors 12-1 to 12-4 that are arranged.

Although the optical fiber sensor that uses the guiding loss of light has been described as the bending sensor according to the present embodiment, it is also possible to use other optical fiber sensors in which, for example, fiber gratings are used for the bending detectors 5-1 to 5-4. Moreover, the fiber-shaped sensors are incorporated to detect bend at multiple points in the configuration shown in FIG. 6. However, (although a detailed configuration principle is not shown) these bending detectors 5-1 to 5-4 may be configured to be integrated by a common optical fiber so that separate detection for each bending detector is possible.

The bending sensor is not limited to the bending sensor that uses the optical fiber. For example, the bending sensor also includes strain sensors that are distributed and arranged, an acceleration sensor, a gyro-sensor, and wireless elements that are distributed and arranged so that their positions can be detected and converted to bending amounts.

Second Embodiment

The second embodiment of the present invention is described below in detail with reference to the drawings. The same parts as those in the first embodiment are not described.

Figure 7:
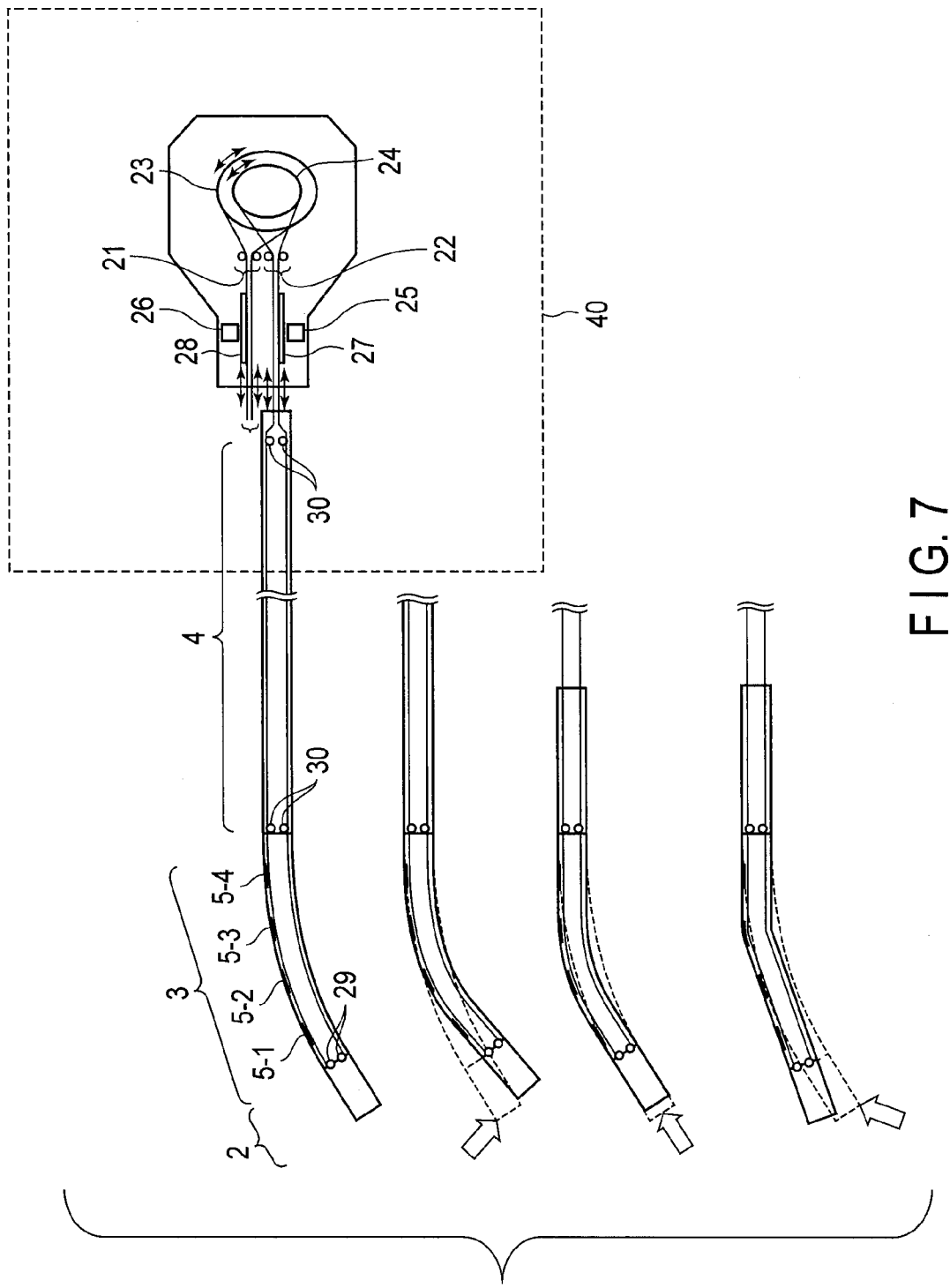
FIG. 7 is a diagram illustrating the principle of external force detection in a tubular insertion device according to a second embodiment of the present invention.

A tubular insertion device according to the present second embodiment includes a bending operation unit 40 so that a tubular insertion portion 1 can be bent by bending operation wires 21 and 22, as shown in FIG. 7. When bending operation knobs 23 and 24 are rotated, one of the bending operation wires 21 and 22 which is connected to the wind-up side of the rotation is pulled. Here, the bending operation wire 21 is a bending operation wire for bending in a left-right (LR) direction, and the bending operation knob 23 is a bending operation knob for a bending operation in the left-right (LR) direction. The bending operation wire 22 is a bending operation wire for bending in an up-down (UD) direction, and the bending operation knob 24 is a bending operation knob for a bending operation in the up-down (UD) direction. The bending operation wires 21 and 22 are coupled to a clasp 29 of a distal rigid portion 2 of the tubular insertion portion 1 via a guide roller 30. This permits the bending amount of the tubular insertion portion 1 to be effected by the rotation of the bending operation knobs 23 and 24. Thus, the bending operation wires 21 and 22 function as the bending operation unit for the operator to effect the bending condition of the tubular insertion portion 1. Although the configurations for operations in the up-down (UD) direction and in the left-right (LR) direction perpendicular to the UD direction as the bending directions are shown in FIG. 7, wires and detection sensors for the LR direction are not shown, for clarity.

Here, the bending operation unit 40 has bending operation detection sensors respectively comprising encoder heads 25 and 26 and encoder scales 27 and 28 that face the encoder heads 25 and 26 for the UD direction and the LR direction to detect the movements, that is, operation amounts of the bending operation wires 21 and 22. The encoder scales 27 and 28 are fixed to the bending operation wires 21 and 22, and the encoder heads 25 and 26 are fixed to the housing of the bending operation unit 40. Thus, when the bending operation knobs 23 and 24 are rotated, the encoder heads 25 and 26 detect the movements of the bending operation wires 21 and 22, so that the total bending angle of a bending portion 3 of the tubular insertion portion 1 can be estimated.

An example of a signal processing algorithm for detecting the external force is now described in detail. The same parts as those in the first embodiment are not described.

Figure 8:
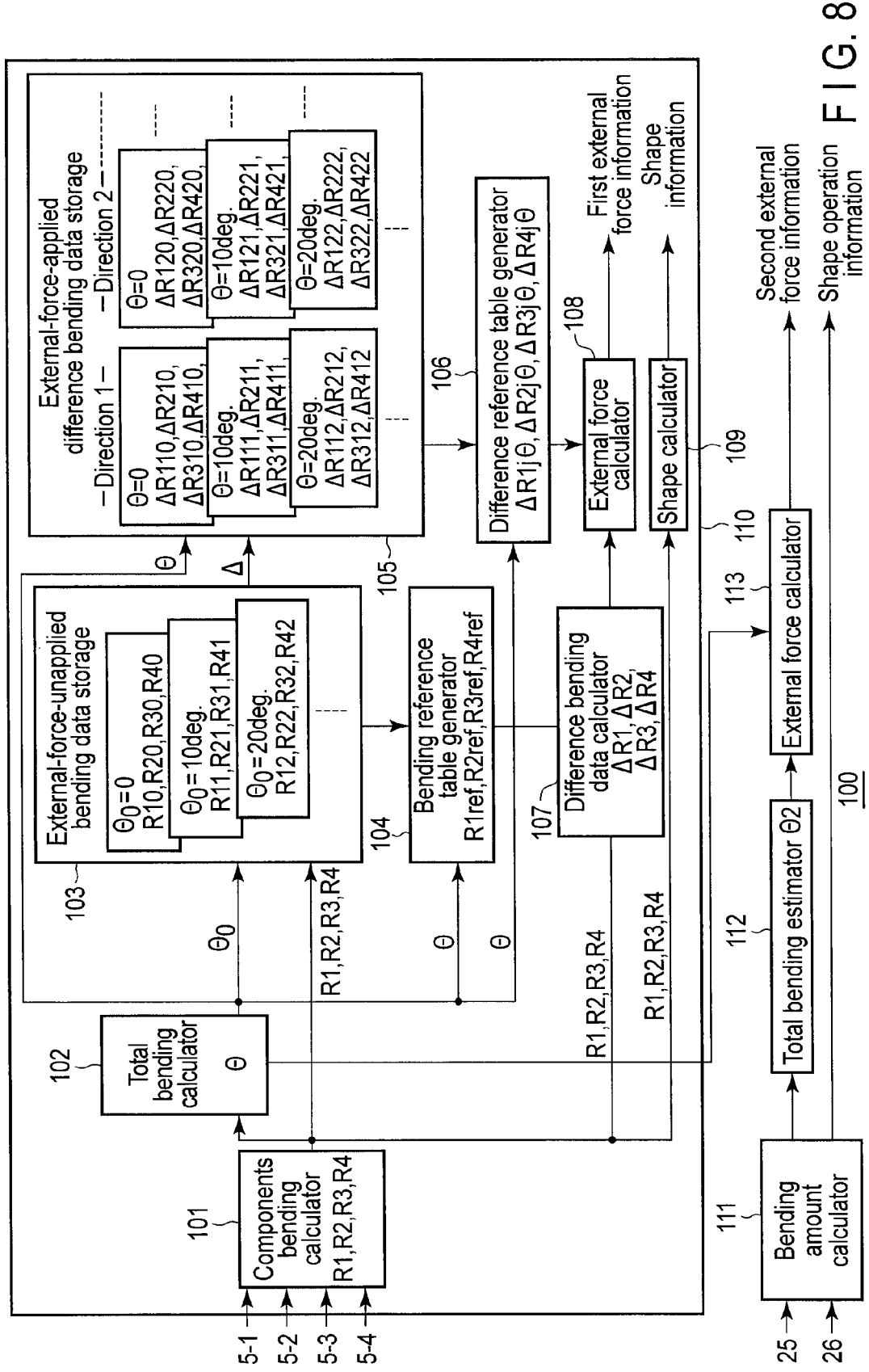
FIG. 8 is a diagram showing the configuration of an operation support information calculating unit in the tubular insertion device according to the second embodiment.

As shown in FIG. 8, an operation support information calculating unit 100 according to the present embodiment comprises a bending amount calculator 111, a total bending estimator 112, and an external force calculator 113, in addition to the components in the first embodiment described above.

The input of the bending amount calculator 111 is connected to the encoder heads 25 and 26 of the bending operation detection sensors. The output of the bending amount calculator 111 is connected to the total bending estimator 112. The output of the bending amount calculator 111 is output to the outside of the operation support information calculating unit 100 as shape operation information. The output of the total bending estimator 112 is connected to the external force calculator 113. The output of a total bending calculator 102 is also connected to the external force calculator 113. The output of the external force calculator 113 is output to the outside of the operation support information calculating unit 100 as second external force information. The output of an external force calculator 108 is output to the outside of the operation support information calculating unit 100 as first external force information. That is, the operation support information calculating unit 100 according to the present second embodiment outputs more than one piece of external force information.

The bending amount calculator 111 can detect, for example, pulling amounts of the bending operation wires 21 and 22 from output signals of the encoder heads 25 and 26, and outputs the pulling amounts as the shape operation information regarding the shape operation of the tubular insertion portion 1.

If an empirical formula is previously formed by use of this value, the total bending estimator 112 can obtain an estimated total bending angle θ2. Although the bending angle intended by the bending operation unit 40 is provided as the estimated total bending angle θ2 by the total bending estimator 112, the actual total bending angle will be an angle different from the estimated total bending angle θ2 because of the external force. This difference can be used to provide the direction and magnitude of the external force. More specifically, it is possible to estimate the current external force F as the second external force information by comparing the current total bending angle θ calculated by the total bending calculator 102 with the estimated total bending angle θ2 obtained by the total bending estimator 112, and multiplying the ratio therebetween by the external force Fo previously set when data is stored in the above-mentioned external-force-applied difference bending data storage 105.

In this way, it is possible to obtain operation support information including the first external force information and the second external force information regarding the external force F applied to the tubular insertion portion 1, shape information regarding the shape of the tubular insertion portion 1, and the shape operation information regarding the shape operation of the tubular insertion portion 1.

The first external force information and the second external force information can be separately used, as the case may be. For example, although a large database and a highly functional calculating device are required to obtain the first external force information, the first external force information is advantageous when information regarding the bending operation unit 40 cannot be obtained. On the other hand, the second external force information does not require a large database and a highly functional calculating device and is therefore suited to a compact device, but requires a configuration to acquire the information regarding the bending operation unit 40. Otherwise, it is possible to separately use or simultaneously use the first external force information and the second external force information in various respects, such as for accuracy and detection speed. Thus, the operation support information calculating unit 100 according to the present second embodiment functions as an operation support information calculator capable of calculating the detection information in the bending operation detection sensors and the detection information in the bending sensors in combination and thereby extracting operation support information including more than one piece of external force information regarding the external force applied to at least the tubular insertion portion 1, and selecting or simultaneously using more than one piece of external force information.

While the present invention has been described above in connection with the embodiments, it should be understood that the present invention is not limited to the embodiments described above and various modifications and applications can be made within the spirit of the invention.

For example, the four bending detectors 5-1, 5-2, 5-3, and 5-4 are arranged as in the embodiments described above. However, it should be understood that the number of bending detectors is not limited to four.

In FIG. 1F to FIG. 1H, the bending detectors 5-1 to 5-4 are aligned on the upper side in the longitudinal direction of the bending portion 3, and an external force in the direction of the sheets is detected. However, if the bending detectors 5-1 to 5-4 are aligned on the lateral side in the longitudinal direction, an external force in a direction perpendicular to the sheets can be detected. Moreover, if the bending detectors 5-1 to 5-4 are respectively aligned on the upper side and the lateral side, an external force can be two-dimensionally detected in a paper sheet direction and the perpendicular direction.

Steps S115 and S116 and step S117 shown in FIG. 4 may be processed in reverse order, or may be processed in parallel. In a similar way, steps S115 to S119 and step S120 may be processed in reverse order, or may be processed in parallel.

A software program that enables the functions of the operation support information calculating unit 100 can be provided to a computer so that the computer performs this program to enable the functions described above.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A tubular insertion device comprising:
a tubular insertion portion including a flexible portion in a predetermined part;

bending sensors distributed and arranged in the flexible portion; and an operation support information calculating unit configured to calculate distribution of a bending amount of the flexible portion and to extract operation support information including at least first external force information regarding an external force applied to the tubular insertion portion based on the distribution of the bending amount by a combinational calculation based on detection information from the bending sensors.

2. The tubular insertion device according to claim 1, wherein the operation support information calculating unit performs a calculation to extract a magnitude and/or a direction of the external force as the first external force information in accordance with the detection information based on a difference of the detection information from the bending sensors between a condition in which no external force is applied to the tubular insertion portion and a condition in which the external force is applied to the tubular insertion portion.

3. The tubular insertion device according to claim 2, wherein the operation support information calculating unit has a function of storing, as external-force-unapplied bending detection information, the detection information from the bending sensors in the condition in which no external force is applied to the tubular insertion portion, and estimating the external force applied to the tubular insertion portion by referring to the stored external-force-unapplied bending detection information.

4. The tubular insertion device according to claim 2, wherein the operation support information calculating unit has a function of storing, as bending detection information, the detection information from the bending sensors in the condition in which no external force is applied to the tubular insertion portion and the detection information from the bending sensors in a condition in which an external force of a predetermined direction and a predetermined magnitude is applied to the tubular insertion portion, and estimating the external force applied to the tubular insertion portion by referring to the stored bending detection information.

5. The tubular insertion device according to claim 1, wherein
the flexible portion of the tubular insertion portion includes parts different in flexibility along an insertion direction, and
the bending sensors are more densely arranged in more flexible parts than in less flexible parts, or bending detectors of the bending sensors are continuously arranged.

6. The tubular insertion device according to claim 1, wherein the operation support information calculating unit calculates, as the operation support information, shape information regarding a shape of the tubular insertion portion by a combinational calculation based on the detection information from the bending sensors, in addition to the first external force information.

7. The tubular insertion device according to claim 1, further comprising:
a bending operation unit for an operator to effect a bending condition of the tubular insertion portion; and
a bending operation detection sensor configured to detect an operation amount of the bending operation unit,
wherein the operation support information calculating unit extracts, as the operation support information, at least second external force information regarding an external force applied to the tubular insertion portion by a combinational calculation based on detection information from the bending operation detection sensor and the detection information from the bending sensors, in addition to the first external force information.

8. The tubular insertion device according to claim 7, wherein the operation support information calculating unit performs a calculation to extract a magnitude and/or a direction of the external force as the first external force information in accordance with the detection information based on a difference of the detection information from the bending sensors between a condition in which no external force is applied to the tubular insertion portion and a condition in which the external force is applied to the tubular insertion portion.

9. The tubular insertion device according to claim 8, wherein the operation support information calculating unit has a function of storing, as external-force-unapplied bending detection information, the detection information from the bending sensors in the condition in which no external force is applied to the tubular insertion portion, and estimating the external force applied to the tubular insertion portion by referring to the stored external-force-unapplied bending detection information.

10. The tubular insertion device according to claim 8, wherein the operation support information calculating unit has a function of storing, as bending detection information, the detection information from the bending sensors in the condition in which no external force is applied to the tubular insertion portion and the detection information from the bending sensors in a condition in which an external force of a predetermined direction and a predetermined magnitude is applied to the tubular insertion portion, and estimating the external force applied to the tubular insertion portion by referring to the stored bending detection information.

11. The tubular insertion device according to claim 7, wherein
the flexible portion of the tubular insertion portion includes parts different in flexibility along an insertion direction, and
the bending sensors are more densely arranged in more flexible parts than in less flexible parts, or bending detectors of the bending sensor are continuously arranged.

12. The tubular insertion device according to claim 7, wherein the operation support information calculating unit calculates, as the operation support information, shape information regarding a shape of the tubular insertion portion by a combinational calculation based on the detection information from the bending sensors, in addition to the first external force information and the second external force information.

13. The tubular insertion device according to claim 12, wherein the operation support information calculating unit calculates, as the operation support information, shape operation information regarding a shape operation of the tubular insertion portion by a calculation based on the detection information from the bending operation detection sensor, in addition to the first external force information, the second external force information, and the shape information.

14. A tubular insertion device comprising:
a tubular insertion portion including a flexible portion in a predetermined part;
bending sensors distributed and arranged in the flexible portion;
a bending operation unit for an operator to effect a bending condition of the tubular insertion portion;
a bending operation detection sensor configured to detect an operation amount of the bending operation unit; and
an operation support information calculating unit configured to calculate distribution of a bending amount of the flexible portion and to extract operation support information including at least more than one piece of external force information regarding an external force applied to the tubular insertion portion based on the distribution of the bending amount by a combinational calculation based on detection information from the bending operation detection sensor and detection information from the bending sensors, and select or simultaneously use the external force information.

15. A tubular insertion device comprising:
a tubular insertion portion including a flexible portion in a predetermined part;
a shape sensor which is disposed in the flexible portion and which detects a bending condition of the whole flexible portion; and
an operation support information calculating unit configured to calculate distribution of a bending amount of the flexible portion and to extract operation support information including at least external force information regarding external force applied to the tubular insertion portion based on the distribution of the bending amount by a combinational calculation based on detection information from the shape sensor in a condition in which no external force is applied to the tubular insertion portion and detection information from the shape sensor in a current condition.

\* \* \* \* \*